United States Patent
Wei et al.

(10) Patent No.: US 9,984,456 B2
(45) Date of Patent: May 29, 2018

(54) METHOD AND SYSTEM FOR LABELING HEPATIC VASCULAR STRUCTURE IN INTERACTIVE LIVER DISEASE DIAGNOSIS

(75) Inventors: Guo-Qing Wei, Plainsboro, NJ (US); Li Fan, Belle Mead, NJ (US); Feng Ma, Pennington, NJ (US); Jianzhong Qian, Princeton Junction, NJ (US); Cheng-Chung Liang, West Windsor, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 1253 days.

(21) Appl. No.: 11/474,505

(22) Filed: Jun. 26, 2006

(65) Prior Publication Data

US 2007/0055455 A1    Mar. 8, 2007

Related U.S. Application Data

(63) Continuation-in-part of application No. 11/105,961, filed on Apr. 14, 2005, now abandoned.
(Continued)

(51) Int. Cl.
   *G06F 19/00* (2018.01)
   *G06F 17/00* (2006.01)
   *G06T 7/00* (2017.01)

(52) U.S. Cl.
   CPC .......... *G06T 7/0012* (2013.01); *G06F 19/321* (2013.01); *G06F 19/3406* (2013.01); *G06F 19/3437* (2013.01); *G06T 2207/30056* (2013.01)

(58) Field of Classification Search
   None
   See application file for complete search history.

(56) References Cited

U.S. PATENT DOCUMENTS 5,644,686 A    7/1997    Hekmatpour
5,891,454 A    4/1999    Wu
(Continued)

FOREIGN PATENT DOCUMENTS

EP    1127547 A1    8/2001
WO    0122363 A2    3/2001
(Continued)

OTHER PUBLICATIONS

Szymczak, A. et al. Proc. SPIE. vol. SPIE-5747, pp. 505-513. 2005.*
(Continued)

*Primary Examiner* — Michael Borin
(74) *Attorney, Agent, or Firm* — Pillsbury Winthrop Shaw Pittman LLP

(57) ABSTRACT

A method for labeling vessel branches forming first and second vessel systems. A 3D image is segmented to obtain vessel branches. First and second root points are then determined. Starting from the first root point, the vessel branches are traced to derive a tracing path and a break point is determined, that separates the tracing path into two portions. A region of interest in the 3D image is determined with respect to the break point, in which center lines are assigned to the first or second vessel system. A 3D cutting structure is generated based on distances measured from points on the center lines to the 3D cutting structure. Graph representations are constructed for the first and second vessel systems. The vessel branches are labeled with different labels based on the graph representations.

14 Claims, 16 Drawing Sheets

Related U.S. Application Data

(60) Provisional application No. 60/693,871, filed on Jun. 24, 2005, provisional application No. 60/561,921, filed on Apr. 14, 2004.

(56) References Cited

U.S. PATENT DOCUMENTS

| | | | |
|---|---|---|---|
| 5,986,662 | A | 11/1999 | Argiro et al. |
| 6,678,399 | B2 | 1/2004 | Doi et al. |
| 6,829,379 | B1 | 12/2004 | Knoplioch et al. |
| 6,944,330 | B2 | 9/2005 | Novak et al. |
| 2002/0028006 | A1 | 3/2002 | Novak et al. |
| 2003/0013959 | A1 | 1/2003 | Grunwald et al. |
| 2003/0095697 | A1 | 5/2003 | Wood et al. |
| 2004/0122704 | A1 | 6/2004 | Sabol et al. |

FOREIGN PATENT DOCUMENTS

| | | |
|---|---|---|
| WO | 2003/101303 | 12/2003 |
| WO | WO 2005/031635 A1 | 4/2005 |

OTHER PUBLICATIONS

Antiga et al. IEEE Transactions on Medical Imaging, vol. 22, No. 5, 2003, p. 674-684.*
Henri et al. Medical Physics, vol. 23, Issue 2, Feb. 1996, pp. 197-204.*
Telea et al. Eurographics—IEEE TCVG Symposium on Visualization (2003) G.-P. Bonneau, S. Hahmann, C. D. Hansen (Editors).*
Bitter et al. IEEE Visualization. Proceedings of the conference on Visualization 2000, Salt Lake City, Utah, United States pp. 45-52.*
Hahn et al. Visualization, 2001. VIS '01, Proceedings , p. 1-8, 2001.*
Van Bemmel et al. IEEE Transactions on Medical Imaging, 22, No. 10, 2003, p. 1224-1234.*
International Search Report and Written Opinion issued in corresponding International Patent Application No. PCT/US2006/024753, dated Jul. 19, 2007.
Selle et al., "Analysis of Vasculature for Liver Surgical Planning," IEEE Transactions on Medical Imaging, Vo. 21, No. 11, Nov. 2002.
Aylward et al., "Registration and Analysis of Vascular Images," International Journal of Computer Vision, pp. 123-138, Kluwer Academic Publishers, 2003, The Netherlands.
Haigron et al., "Depth-Map-Based Scene Analysis for Active Navigation in Virtual Angioscopy," IEEE Transactions on Medical Imaging, vol. 23, No. 11, Nov. 2004.
Giansanti et al., "Imaging System for Retinal Change Evaluation," IPA97, Jul. 15-17, 1997, Conference Publication No. 443, IEE, 1997.
International Search Report and Written Opinion issued in corresponding International Patent Application No. PCT/US2005/012733, dated Apr. 14, 2005.
United States Office Action issued in U.S. Appl. No. 11/105,961, dated Aug. 18, 2009.
Quinlan, J.R., "Induction of Decision Trees", Machine Learning, 1986, pp. 81-106, vol. 1.
Tombropoulos, R., et al., "A Decision Aid for Diagnosis of Liver Lesions on MRI", Proc. Annu. Symp. Comput. Appl. Med. Care, 1993, pp. 439-443, AMIA, Inc.
Ballard et al., A Ladder-Structured Decision Tree for Recognizing Tumors in Chest Radiographs, IEEE Transactions on Computers, vol. C-25, No. 5, May 1976, pp. 503-513.
Office Action dated Jan. 14, 2016 in U.S. Appl. No. 11/105,961.
Office Action dated Oct. 25, 2016 in European Application No. 05736052.1.
Supplementary European Search Report corresponding to European Serial No. 05736052 dated Jan. 30, 2013.
Chinese Office Action corresponding to Chinese Serial No. 200580011415.8 dated Mar. 7, 2012.
United States Office Action issued in U.S. Appl. No. 11/105,961, dated May 26, 2010.
Paupe, C., et al., "A Hypertext Based Diagnostic Systems for Aiding in the Detection of Vibration Defaults of Rotating Machines", IEEE, 1999, pp. 804-809.
Wong, S., et al., "Interactive Query and Visualization of Medical Images of the World Wide Web", SPIE, 1996, pp. 390-401, vol. 2707.
Morizet-Mahoudeaux, P. M., et al, "Toward Hypertext System Based Diagnosis", Ninth International Workshop on Principles of Diagnosis, May 1998, pp. 1-8, USA.
Ballard et al. (IEEE Transactions on Computers, May 1976, pp. 503-513).
Carrillo et al. (IEEE Transactions on Medical Imaging, Mar. 2000, vol. 19, No. 3, p. 175-185).
International Search Report and Written Opinion issued in International Application No. PCT/US2005/012733, dated Apr. 3, 2007.
Office Action dated Apr. 17, 2008 in U.S. Appl. No. 11/105,961.
Office Action dated Apr. 20, 2011 in U.S. Appl. No. 11/105,961.
Office Action dated Apr. 25, 2014 in U.S. Appl. No. 11/105,961.
Office Action dated Jul. 31, 2007 in U.S. Appl. No. 11/105,961.
Office Action dated Nov. 24, 2008 in U.S. Appl. No. 11/105,961.
Office Action dated Sep. 26, 2013 in U.S. Appl. No. 11/105,961.
Supplemental European Search Report issued in International Application No. PCT/US2005/012733, dated Jan. 30, 2013.

* cited by examiner 411            412

METHOD AND SYSTEM FOR LABELING HEPATIC VASCULAR STRUCTURE IN INTERACTIVE LIVER DISEASE DIAGNOSIS

The present invention is a continuation in part of the U.S. patent application Ser. No. 11/105,961, titled "Liver Disease Diagnosis System, Method and Graphical User Interface" filed on Apr. 14, 2005, and claims the benefit under 35 U.S.C. § 119(e) of U.S. Provisional Patent Application No. 60/693,871 filed on Jun. 24, 2005, titled "Interactive Liver Disease Diagnosis Methods" and U.S. Provisional Patent Application 60/561,921 filed on Apr. 14, 2004 titled "System and graphical user interface for liver disease diagnosis", all of which are incorporated by reference herein in their entirety.

BACKGROUND

1. Field of the Invention

The present teaching relates generally to methods and graphical user interface for medical diagnosis. Specifically, the present teaching relates to methods and graphical user interfaces for computer assisted medical diagnosis and systems incorporating the present teaching.

2. Description of Related Art

Early detection of liver cancer has recently become possible due to rapid technical advancement in diagnostic imaging systems. Detection and diagnosis of liver cancer usually involves multiple image acquisitions in, frequently, multiple image modalities. For example, Computerized Tomography (CT) is the most popular modality for earlier liver cancer detection and diagnosis. When CT images are used, up to four phases of images may be acquired for diagnosis purposes. These four phases include plain CT images, arterial phase images, portal venous phase images, and delayed phase images. When CT images are not adequate to assist in reaching a diagnosis, images in other image modalities may also be used. Examples of other modalities include images from Magnetic Resonance Imaging (MRI) or Positron Emission Tomography (PET). When a large amount of data becomes available, there is a need for means to make effective use of such data and to assist physicians or other medical personnel to improve throughput.

BRIEF DESCRIPTION OF THE DRAWINGS

The teaching claimed and/or described herein is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

The present teaching relates to methods and graphical user interfaces for liver disease diagnosis. Methods and graphical user interfaces are disclosed herein that facilitate coordinated retrieval of visual and non-visual data associated with a patient and a liver disease, manipulation of visual/non-visual data to extract diagnostic information, generation of a hierarchical representation for visual and non-visual diagnostic information, interactive exploration of the hierarchy of diagnostic information, and an interactive diagnosis process. Methods and graphical user interfaces for effective visualization of data in different dimensions are also disclosed.

Figure 1:
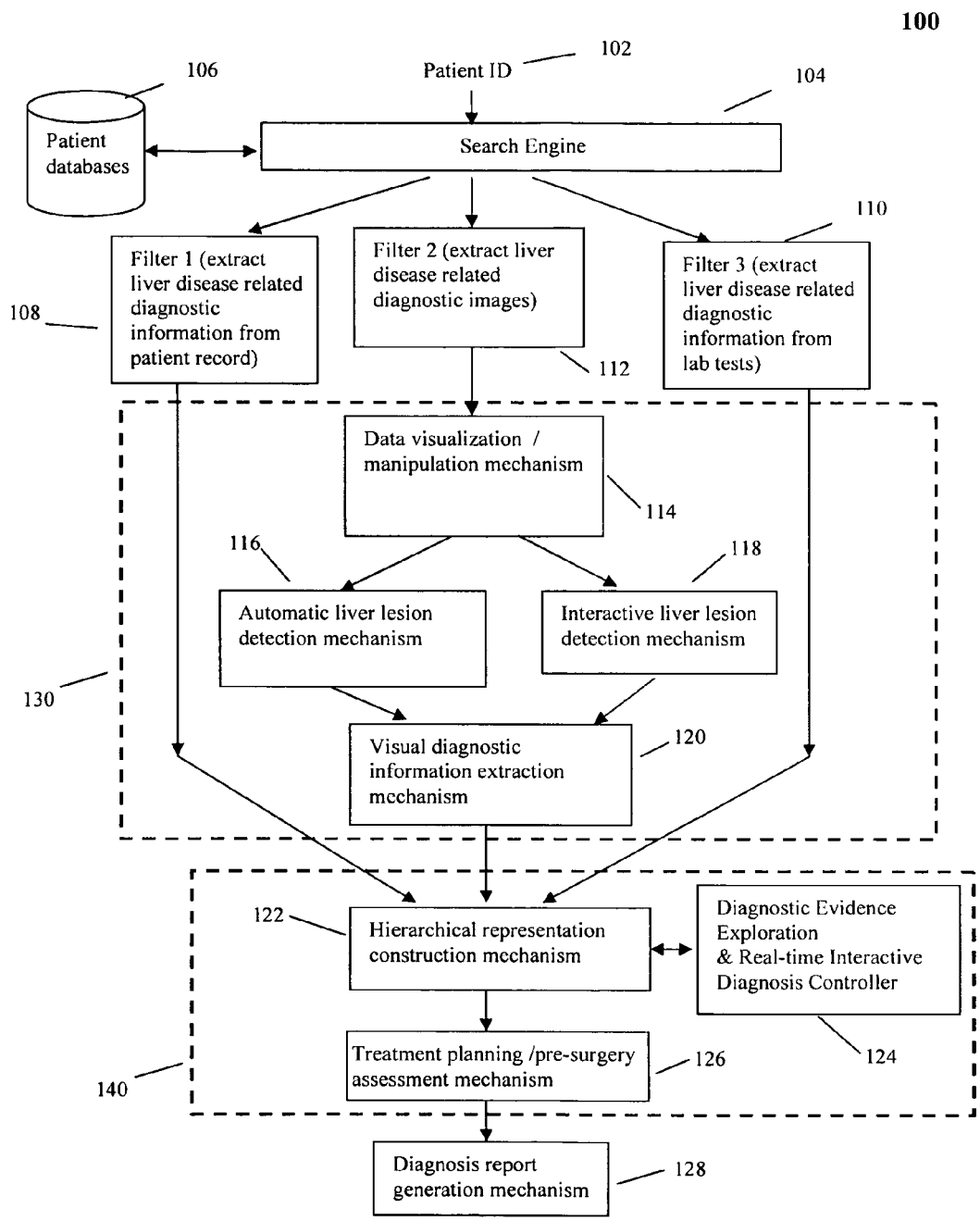
FIG. 1 depicts an exemplary construct of a system for computer assisted liver disease diagnosis, according to an embodiment of the present teaching.

FIG. 1 depicts an exemplary system 100 according to an embodiment of the present teaching. In this exemplary construct, the system 100 comprises a plurality of filters (a filter 1 108, a filter 2 112, and a filter 3 110), a visual data manipulation mechanism 130, a liver disease diagnosis mechanism 140, and a diagnosis report generation mechanism 128. The system 100 may further include a search engine 104 that retrieves information associated with a patient ID 102 from a patient database 106. The search engine 104 may access information stored in the patient database according to the patient ID 102 received. The patient database 106 may be a local data depository or a remote data depository. The patient database 106 may be a single database or multiple databases, which may be located at a single site or distributed at multiple locations across a network. The visual data manipulation mechanism 130 may further comprise a data visualization/manipulation mechanism 114, an automatic liver lesion detection mechanism 116, an interactive liver lesion detection mechanism 118, and a visual diagnostic information extraction mechanism 120. The liver disease diagnosis mechanism 140 may further comprise a hierarchical representation construction mechanism 122, a diagnostic evidence exploration & real-time interactive diagnosis controller 124, and a treatment planning/pre-surgery assessment mechanism 126.

Figure 2A:
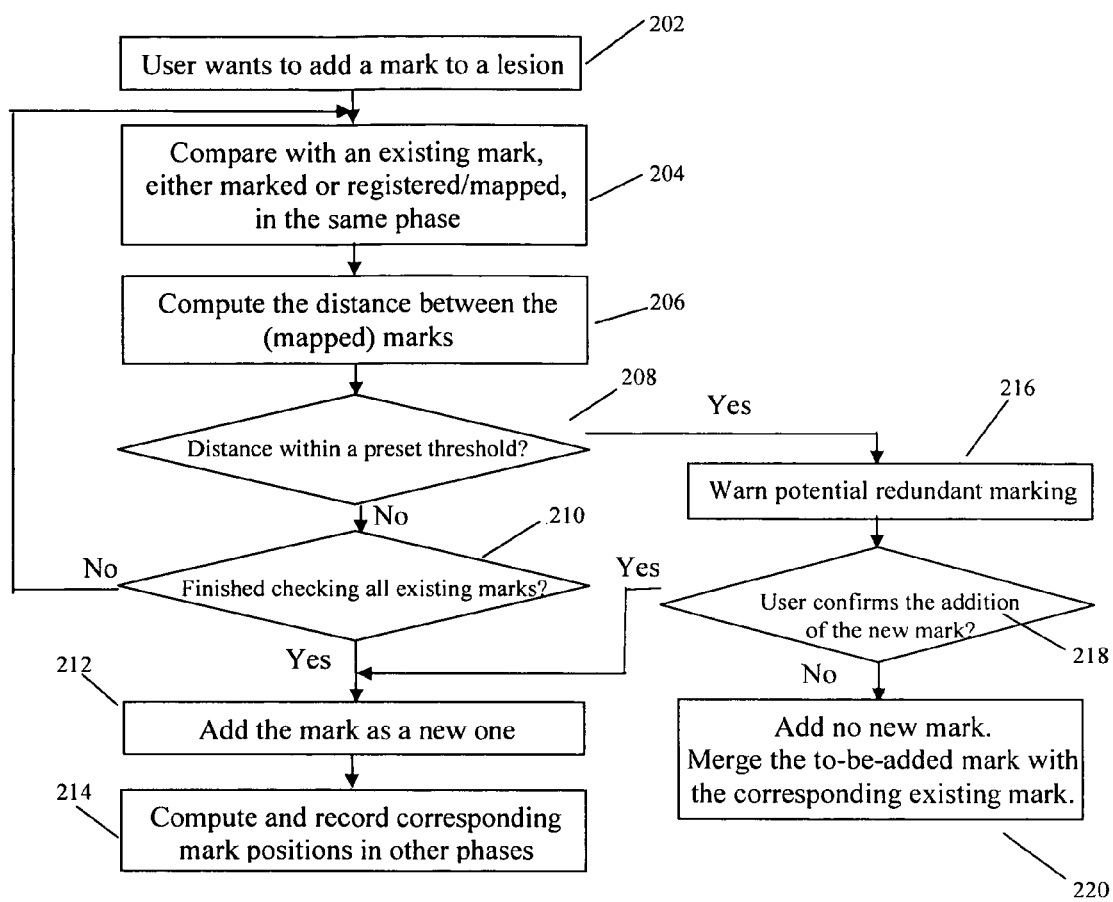
FIG. 2(a) depicts an exemplary flow chart of a marking enforcement means.

One of the functionalities supported by the visual data manipulation mechanism 114 is that user may mark a contour of a detected lesion for further analysis. However, a lesion may be marked multiple times when multiple-phase volumetric data, such as CT or MRI, is used for diagnosis. First, a lesion may span multiple image slices so that user may double mark it on a different slice. Second, a lesion may be visible on multiple phases so that user may mark it multiple times on various phases. To avoid any confusion arising from multiple-marking, a marking enforcement means is deployed. FIG. 2(a) shows an exemplary flow chart of the marking enforcement means 200-a. User marks in one phase, as denoted by step 202, its distance to all recorded marks (the distance between a peripheral edge of the newly marked contour and the peripheral edges of the recorded contours), either marked in the same phase or mapped/registered into the same phase, are measured at steps 204, 206. In cases where an existing mark is made in a different phase, the two marks to be compared may be mapped into one phase volume, before the distance is computed.

In step 208, the computed distance between the newly marked contour and an existing contour is compared with a preset threshold value. If there is more than one existing contour in the database, the system compares the newly marked contour with all the existing contours as indicated by step 210. If the closest distance between the newly marked contour and the existing contours is greater than the preset threshold value, the newly marked contour is saved in the database as a new mark at step 212. The system then computes and records corresponding mark positions in other phases at step 214.

Figure 2B:
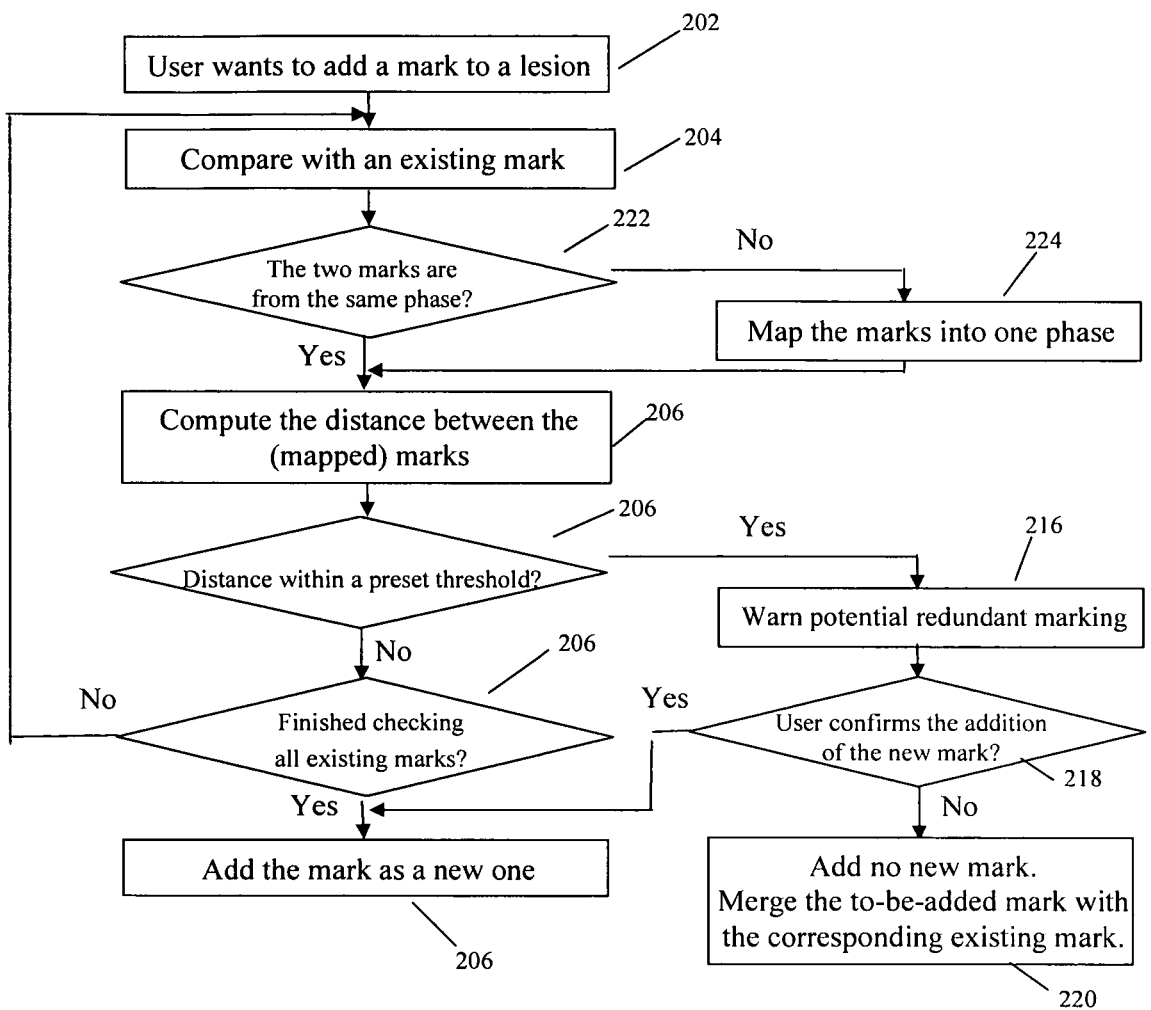
FIG. 2(b) depicts an alternative exemplary flow chart of a marking enforcement means.

If the distance is within the preset threshold value, it is likely that this lesion to be marked has been marked previously. A warning message may then pop up for user's attention at step 216. The lesion mark may be added as a new mark if the user chooses so at step 212, 214. Otherwise, it may be merged with the corresponding existing mark at step 220. If the marked lesion is considered as a new lesion, its corresponding locations in other phases may be identified as the same lesion using certain mapping/registration techniques and recorded. An exemplary method for mapping lesion positions in different image phases may be the spatial-temporal registration technique disclosed in the U.S. patent application Ser. No. 11/105,961. A complete set of lesion marks, whichever phase they are marked in, can be made available for each phase and may be displayed as needed. An alternative exemplary flow chart of the marking enforcement means is shown in FIG. 2(b). In this alternative embodiment, in which a complete set of lesion marks is not necessary for each phase, the mark to be added and the existing marks may be mapped/registered into one same phase (as denoted by steps 222 and 224 in FIG. 2(b)) before a distance is computed.

Figure 3A:
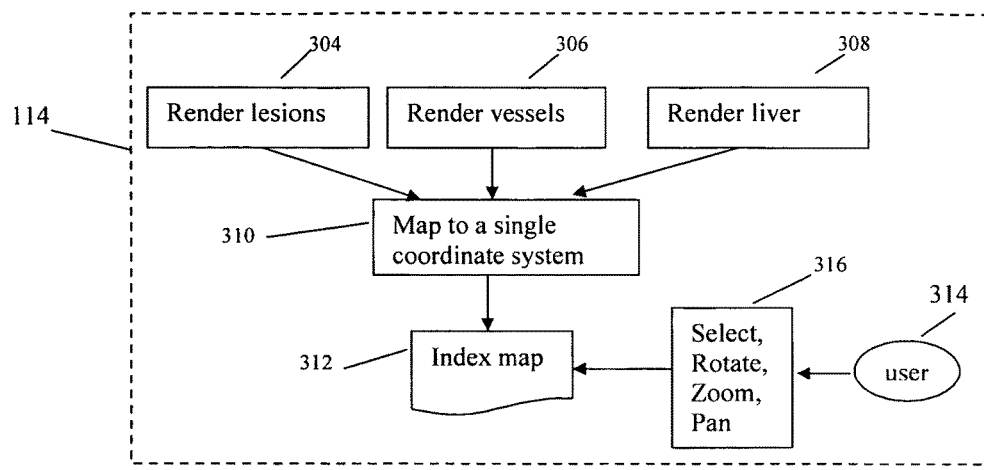
FIG. 3(a) shows an exemplary flowchart for constructing an index map.
Figure 3B:
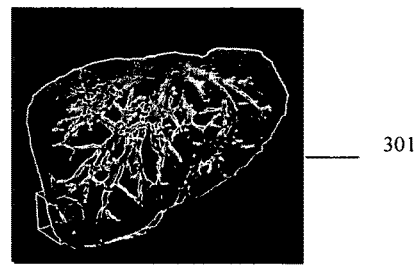
FIG. 3(b) depicts an exemplary index map.
Figure 3C:
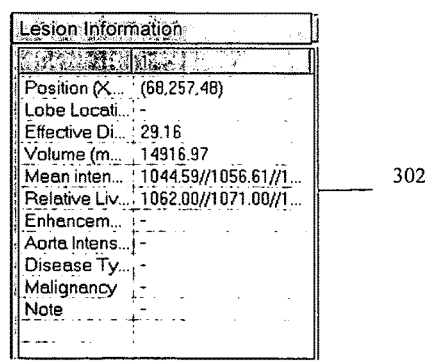
FIG. 3(c) shows a lesion information table associated with a lesion in the index map.

The visual data manipulation mechanism 114 may facilitate navigation of marked lesions. FIG. 3(a) illustrates an exemplary presentation, according to one embodiment of the present teaching. Lesions may be rendered in 3D at step 304. Similarly, vascular structures, including but not limited to, hepatic vein and portal vein, may by rendered in 3D at step 306. Liver parenchyma and lobe segments may also be rendered in 3D at step 308. These 3D structures may be displayed in different colors to distinguish from one another. Since lesions may be marked in different phases, a mapping of such marked lesions into one phase may be performed at step 310. A lesion index map, 312, may then be generated by superimposing different structures in one display. A user, 314, may operate and manipulate the display based on the index map. For example, the view of the 3D rendering may be rotated, zoomed, at step 316. A mouse click on a lesion rendered in the lesion index map may result in a refreshed display of information relevant to the clicked lesion. Such information may include, but is not limited to, lesion diagnostic information displayed in a lesion information table and slice images of different phases displayed, e.g., the corresponding axial, saggital and coronal slice images. FIG. 3(b) illustrates an exemplary lesion index map 301. FIG. 3(c) shows an exemplary lesion information table associated with a lesion.

After a lesion is marked or selected, more detailed analysis may be performed via visual diagnostic information extraction mechanism 120. FIG. 4 illustrates an exemplary embodiment of diagnostic information extraction. User may segment the boundary of a lesion using either automatic segmentation or manual drawing methods, at step 440. The lesion boundary may be overlaid on the original image slice, at step 442. The corresponding lesion boundaries in other phases may be automatically computed by mapping from the segmented boundary, at step 444. The mapped boundaries may be overlaid on the corresponding phase images, at step 446. After lesion segmentation, aorta may be segmented either automatically or manually, at step 448. At step 450, diagnostic information may then be extracted from the segmented lesion and aorta, and such information from multiple phases may be fused based on their corresponding segmentation results. Diagnostic information may include, but not be limited to, mean and standard deviation of the absolute intensity value of a lesion in each phase, the intensity difference between a lesion and liver parenchyma in each phase, the absolute aorta intensity in each phase, the intensity difference between the lesion and aorta in each phase, and the enhancement pattern of a lesion across different phases, etc. Such information may be presented in various ways including, but not limited to, graph, plots, tables, and text, at step 452. The lesion segmentation and aorta segmentation results may be adjusted at step 454. After each adjustment, relevant lesion information may be updated at step 452 accordingly. A segmented lesion may be rendered in a 3D space so that its spatial relationship with respect to, e.g., liver and vascular structures may be visualized at step 456. User may interact with the display by zooming or rotating the display.

Figure 4A:
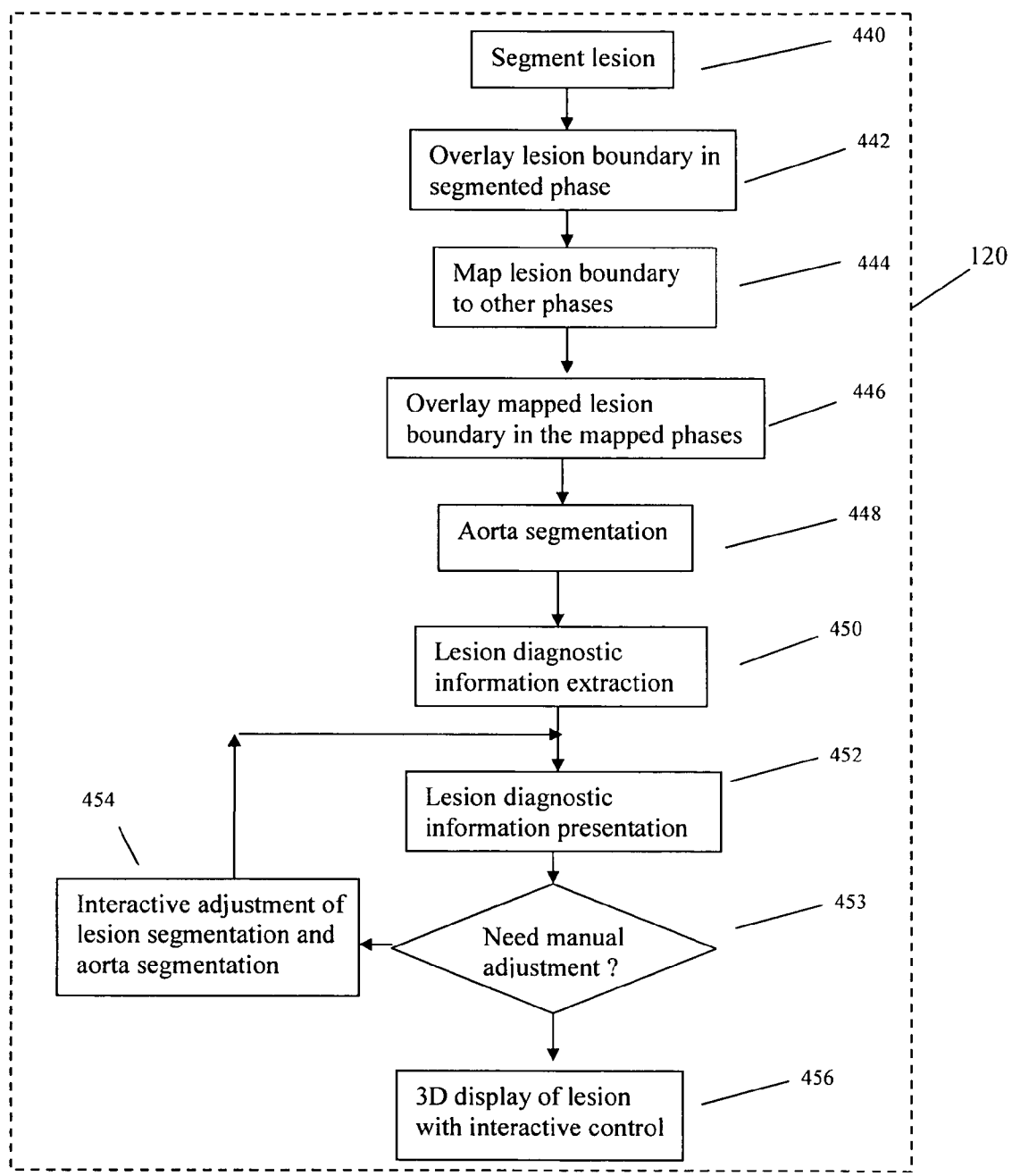
FIGS. 4(a) depicts an exemplary flowchart for lesion segmentation, aorta segmentation, and lesion information presentation.
Figure 4B:
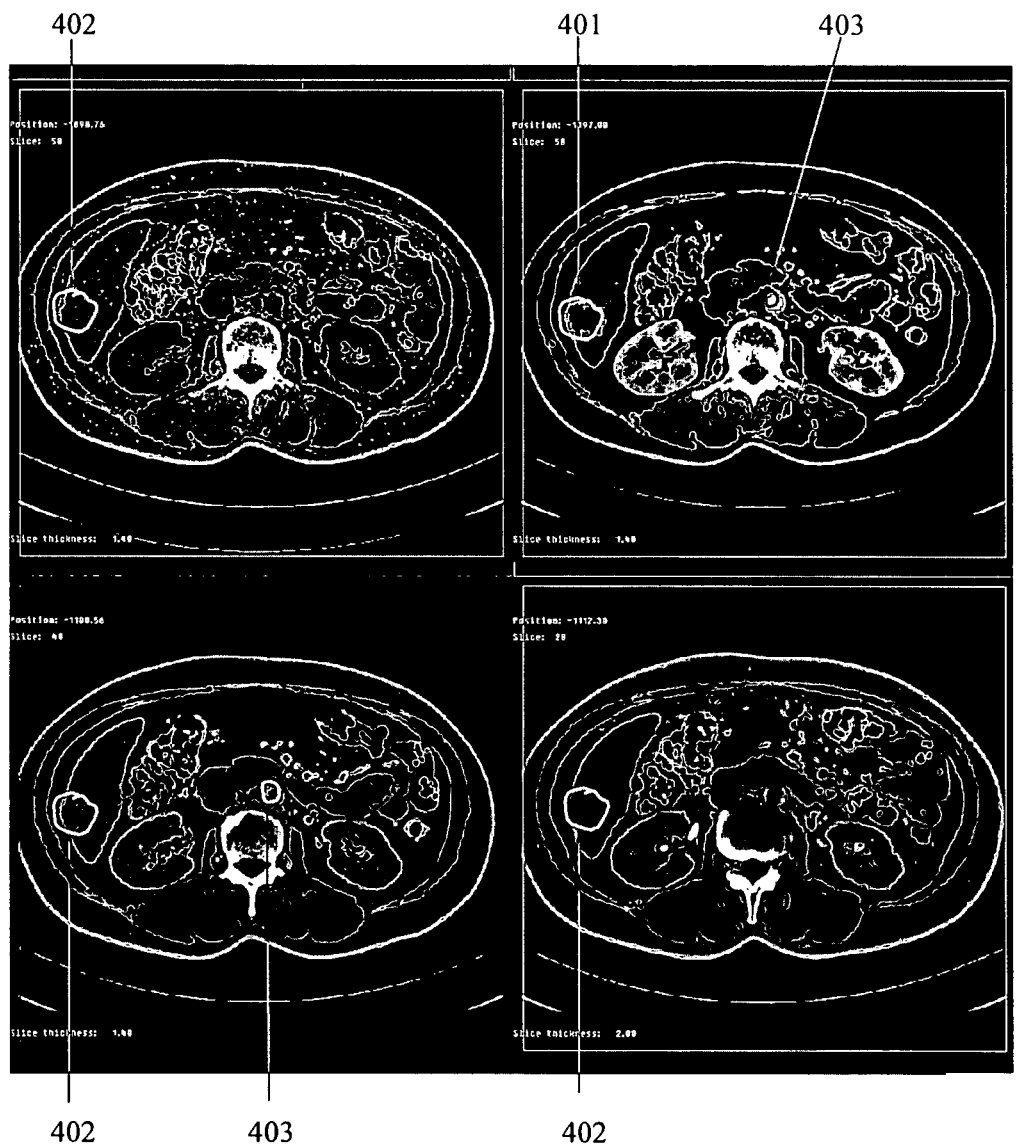
FIGS. 4(b) depicts an exemplary manner of presenting lesion segmentation results and related information.
Figure 4C:
FIG. 4(c) depicts an exemplary presentation of lesion segmentation results in 3D.
Figure 4D:
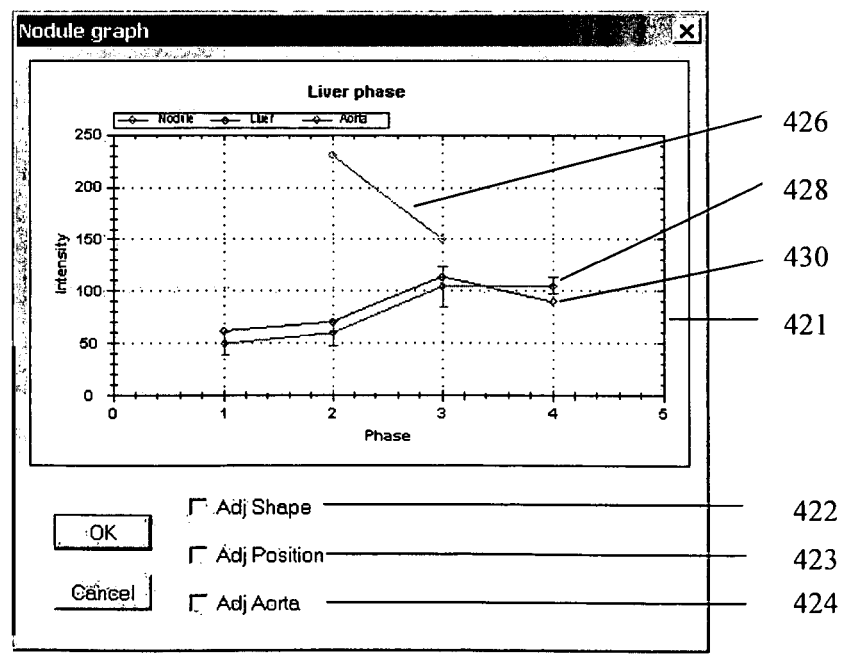
FIG. 4(d) depicts some exemplary means of lesion diagnostic information presentation and controls of information extraction.

FIG. 4(b) shows an example of lesion segmentation and aorta segmentation. Overlay 401 represents the original segmented lesion boundary, while boundaries 402 represents mapped boundaries in other phases. The aorta boundaries are shown as 403 in two phases. FIG. 4(c) shows a 3D display of a lesion. Display 411 is a local view of the 3D display, while display 412 is a global view of the same display by zooming the local display. FIG. 4(*d*) shows an exemplary information presentation performed at step 452. Display 421 is a graph representing the enhancement change of the liver 430, aorta 426, and the lesion 428 across the phases. Display 422 is a control for manual adjustment of lesion size. A sliding bar may pop up (not shown) that allows user to adjust the segmented lesion size. Display 423 is a control for adjustment of lesion position in the mapped phases. User may drag and move a computed lesion boundary in the image to an appropriate position. The position resulted from such a drag operation may be used to correct mapping errors. The control 424 is for adjusting aorta segmentation. The shapes and positions of the extracted aorta regions may be edited if the 'adjust aorta information' function 424 is activated. The adjusted results, as well as the corresponding diagnostic information extracted, may be updated accordingly each time an adjustment is made.

Figure 5:
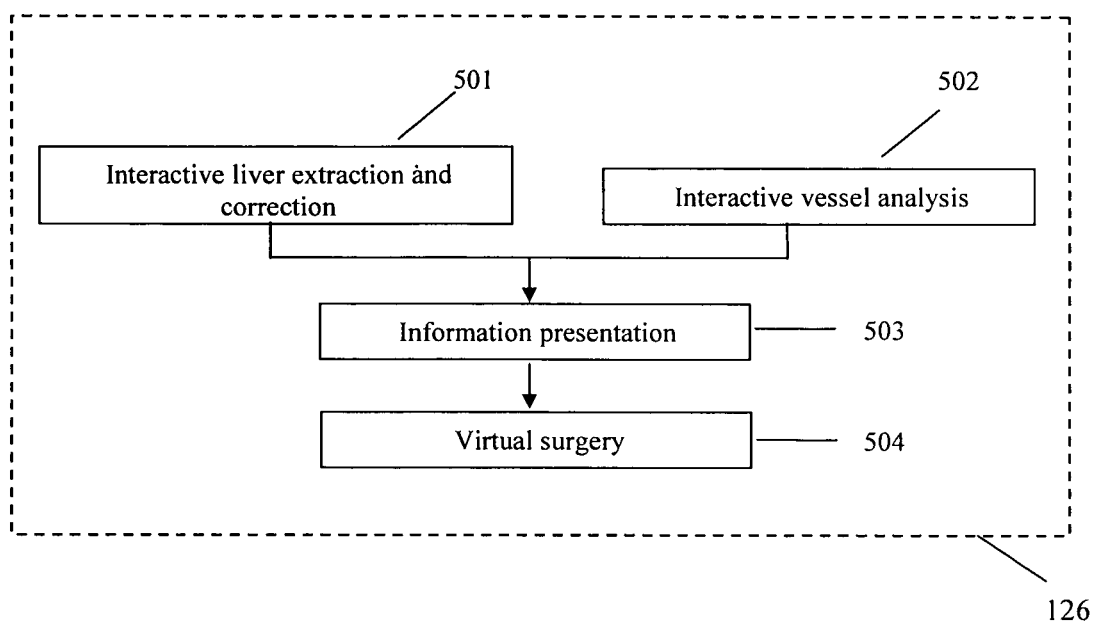
FIG. 5 depicts an exemplary treatment planning/pre-surgery assessment mechanism.

The treatment planning/pre-surgery assessment mechanism 126 is provided to perform treatment planning and pre-surgical assessment with respect to each detected lesion. An exemplary embodiment is shown in FIG. 5, which is provided to facilitate interactive liver extraction correction 501, interactive vessels analysis 502 for precise assessment, in terms of effective presentation of desirable information 503, and functionalities that support virtual surgery 504. Treatment planning may be devised based upon information such as lesion type, attachment pattern of a lesion with respect to a major vessel, and the liver lobe segment in which the lesion resides. Treatment planning may be designed to determine whether a remaining portion of liver will function properly if a part of the liver is to be resected.

Figure 6:
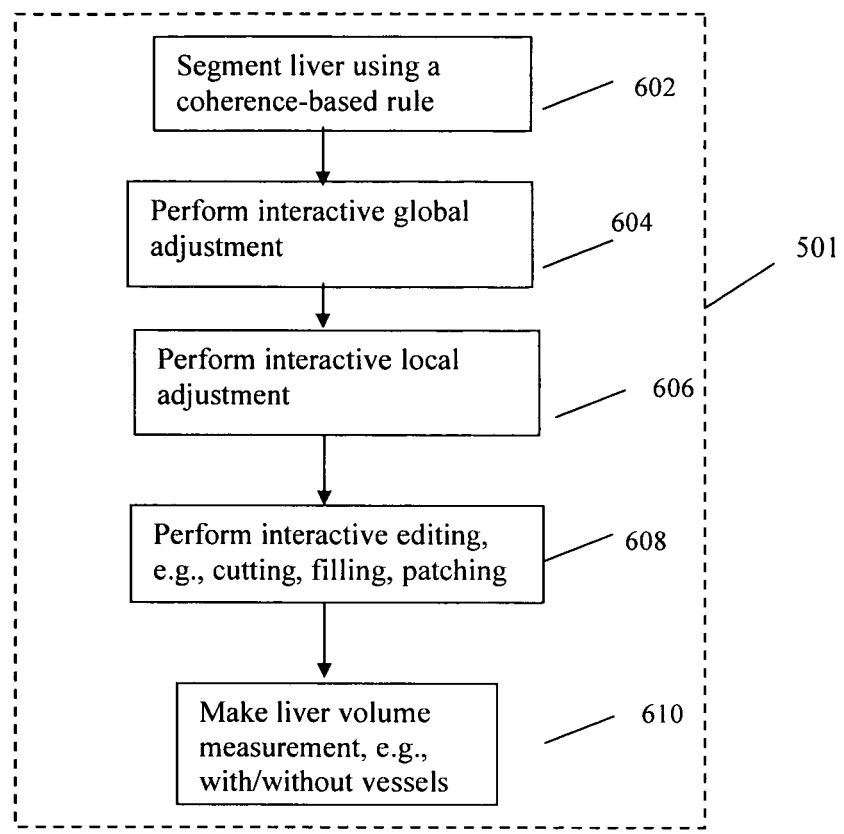
FIG. 6 depicts an exemplary flowchart for interactive liver segmentation.

The interactive liver extraction and correction means 501 facilitates manual correction and guidance of the automatic liver segmentation method. Liver segmentation facilitates extraction of the liver parenchyma from image data. An exemplary embodiment is shown in FIG. 6. Liver parenchyma may be segmented by using an edge-based coherence segmentation method at step 602. The coherence segmentation compares intensity statistics of a growing region with that of pixels at the growing front pixels, and expands the region by admitting adjacent regions that have pixels having similar intensity statistics. A user may change a global threshold value to adjust the size of the segmented region at step 604. Such threshold may correspond to a liver Hounsfield unit. Contours of a segmented liver parenchyma after each adjustment may be overlaid onto an original image to provide a visual reference to users to make possible further adjustment. A user may also make a local adjustment of the segmentation by manually defining a local liver volume to which an adjustable parameter is applicable at step 606. Automatic computation of the local adjustment parameters may be performed based upon different methods, including, but not limited to, shape continuity and local teaching. Shape continuity may be measured by computing a degree of matching between a local segmentation with a global segmentation within the overlapping volume. The best match within the overlapping volume may be chosen as an optimal parameter. In local teaching, a user may input a partial segmentation. A partial segmentation may either be a user-defined liver region or a user-defined liver edge. From such a user-drawn region or liver edge, optimal segmentation parameters may then be computed. The segmented liver may be interactively edited using tools, such as cutting, filling, and patching, at step 608. Based on the liver segmentation, different volume measurements may be computed at step 610, and such measurements may be made: with or without lesions, with or without vessels, or any combination thereof. The volume of a liver region resulted from such editing may be computed either for the cut part or the remaining part.

Figure 7A:
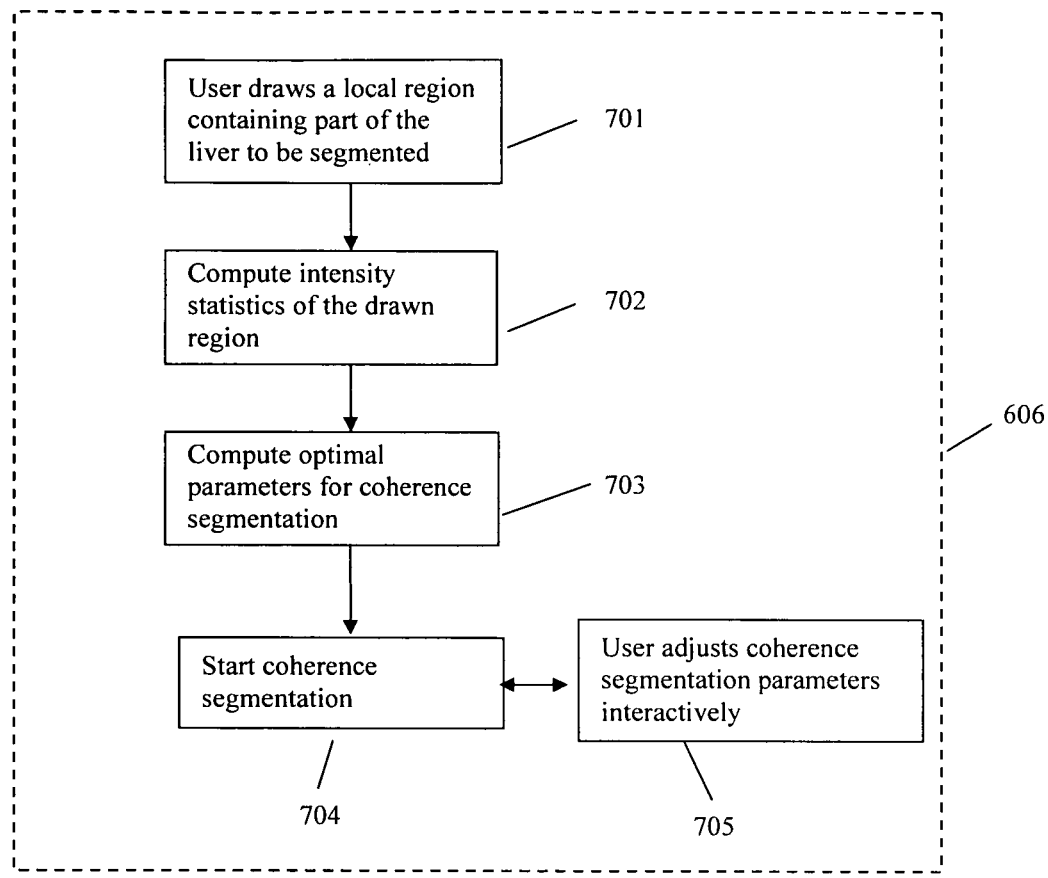
FIG. 7(a) depicts an exemplary local-teaching method for interactive liver segmentation adjustment in terms of user-drawn liver region.
Figure 7B:
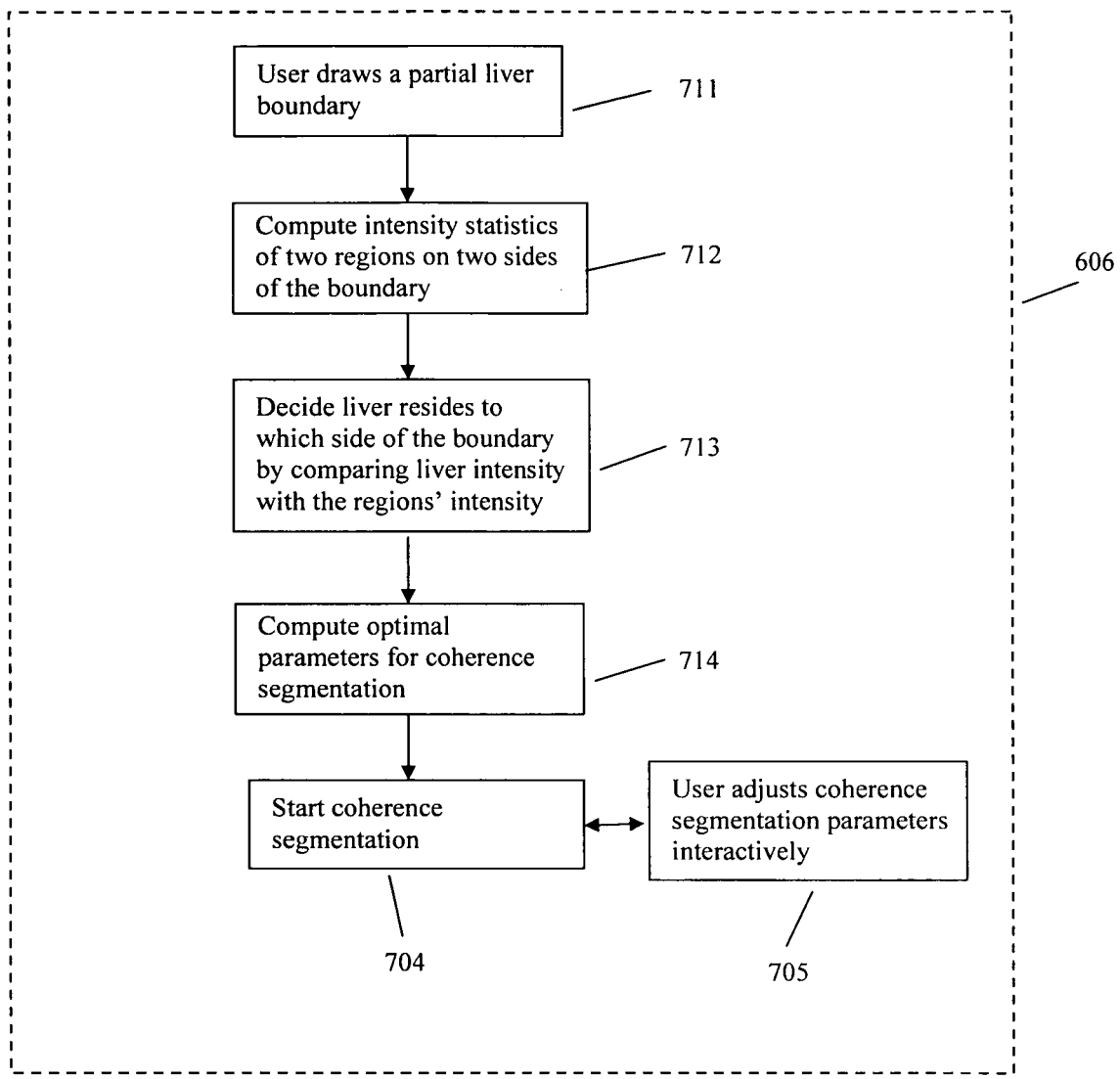
FIG. 7(b) depicts an exemplary local-teaching method for interactive liver segmentation adjustment in terms of user-drawn liver boundary.

FIG. 7(*a*) depicts an exemplary embodiment of interactive local adjustment 606 that facilitates region segmentation. A user may initially draw a region containing part of the liver to be segmented at step 701. The intensity statistics of the drawn region is computed at step 702. Optimal parameters for coherence segmentation are computed at step 703. At step 704, the coherence-based segmentation is performed using the optimal parameters. A user may adjust the coherence segmentation parameters and repeats the segmentation as desired, at step 705.

FIG. 7(*b*) depicts another exemplary embodiment of interactive local adjustment 606 that facilitates region segmentation. Initially a user draws a partial liver boundary at step 711. The intensity statistics of two regions on both sides of the user-drawn boundary are computed at step 712. A decision is made as to which side of the drawn boundary contains liver, which may be achieved by comparing known liver intensity with intensity of the two regions (on the respective sides of the drawn boundary) at step 713. Optimal parameters for coherence liver segmentation may then be determined at step 714. At step 704, the local liver parenchyma may be segmented using such derived optimal parameters. A user may adjust the coherence segmentation parameters and repeats the segmentation as desired, at step 705.

Figure 8:
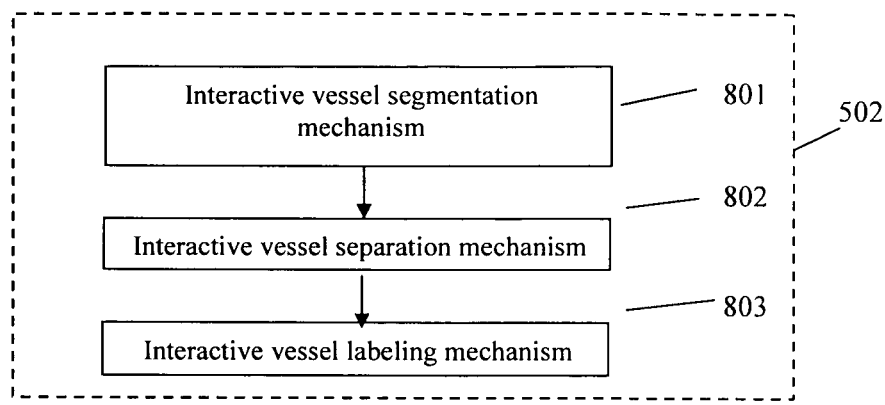
FIG. 8 depicts an exemplary flow chart for interactive vessel analysis.

FIG. 8 depicts an exemplary scheme for vessel analysis 502. Vessel analysis may be performed by a mechanism having three components: interactive vessel segmentation mechanism 801, interactive vessel separation mechanism 802, and interactive vessel branch labeling mechanism 803.

Figure 9:
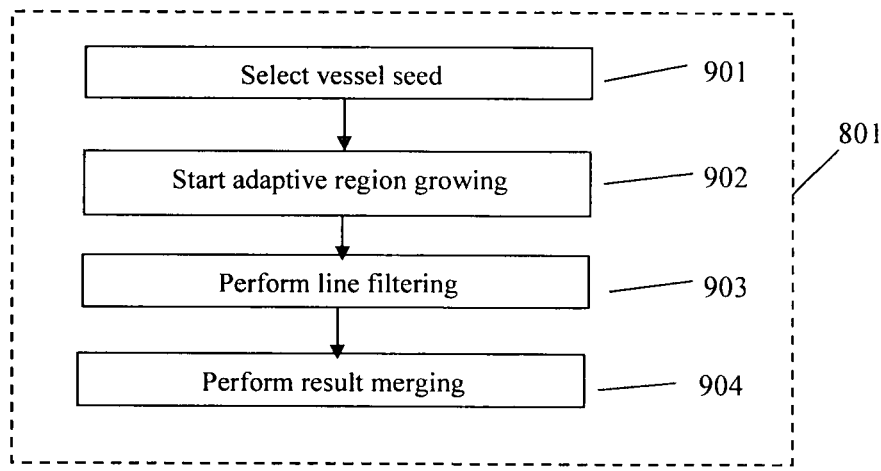
FIG. 9 depicts an exemplary flow chart of vessel segmentation.

In some embodiments, interactive liver vessel segmentation may be performed on images acquired in a portal venous phase if CT images are used. FIG. 9 illustrates an exemplary flow chart of this procedure. Vessel segmentation may start with an automatically or interactively selected point on a main vessel branch, e.g., the main portal vein, at step 901. An intensity based adaptive region growing approach may be applied at step 902, which is followed by a 3D line filtering at step 903. The results obtained from steps 902 and 903 may be further combined to generate a final segmentation result at step 904. The procedure of vessel segmentation is described below in more details.

Intensity based adaptive region growing segmentation mechanism at step 902: Starting with a selected vessel seed point (determined either automatically or manually), region growing may be performed based on voxel intensity level. A threshold of the intensity used in region growing may be adaptively decreased until, e.g., a vessel to liver volume ratio exceeds a certain threshold. The segmentation before the ratio is reached may be identified as a vessel.

Line filtering mechanism at step 903: This algorithm may be used to segment small vessel branches not connected to major vessel branches that are segmented via, e.g., region growing. A line filter is a 3D shape filter used to enhance a 3D tubular structure. At locations where 3D tubular objects such as vessels are present, a high response may be generated in the output of a line filter. Another round of region growing may be applied on the output of 3D line filtering of a volumetric image, so that small vessel branches can be detected.

Combination mechanism at step 904: The above two algorithms may be applied sequentially so that vessels of different sizes may be segmented. Adaptive region growing may be applied to segment major vessel branches while 3D line filtering may be used to extract small vessel branches (such as vessels with a radius less than a pre-defined threshold). In some embodiments, the overall segmentation algorithm may take some user-inputs, e.g., as few seed points to enable adaptive region growing. In other embodiments, no user interaction is needed in line filter segmentation.

Figure 10:
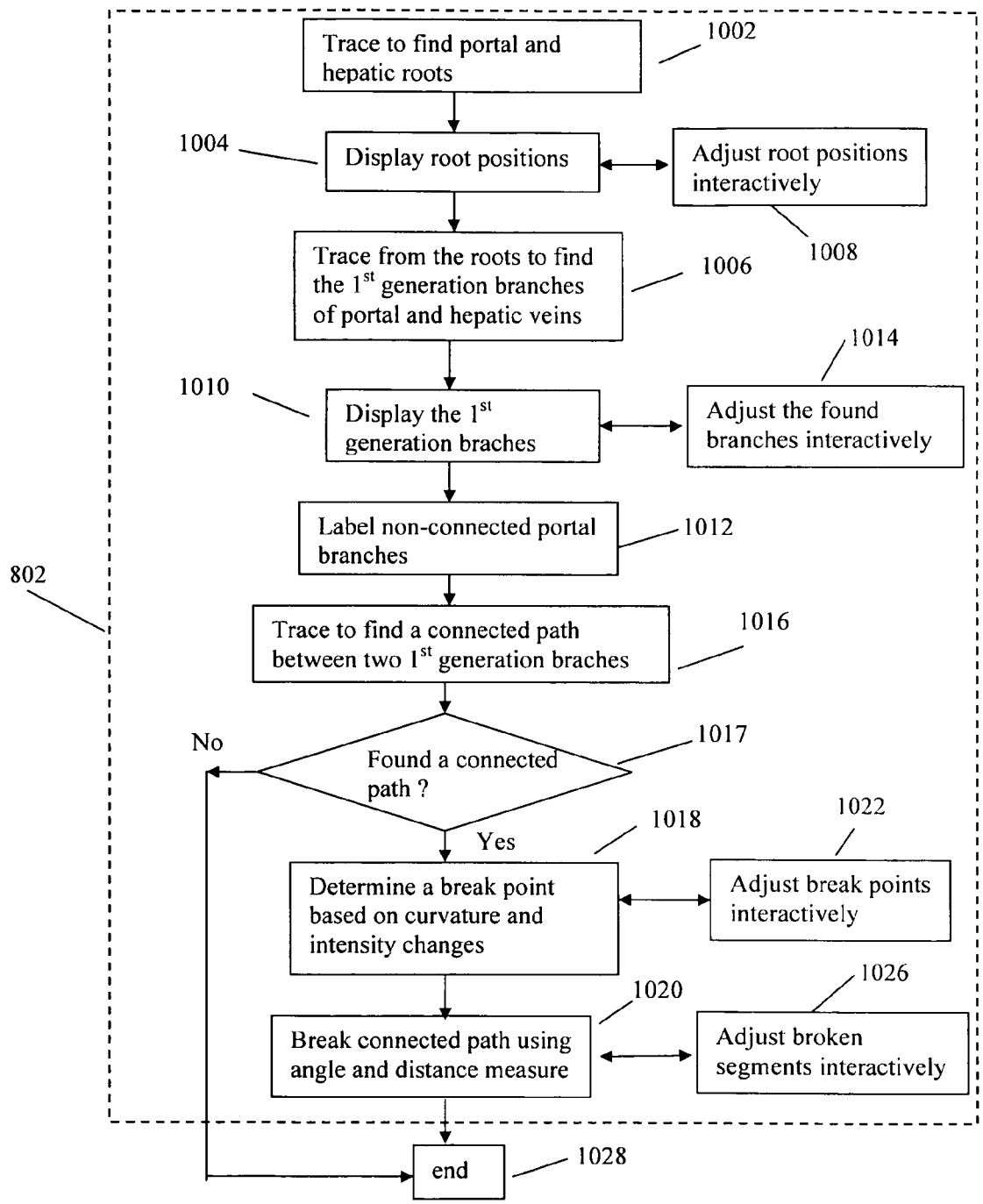
FIG. 10 depicts an exemplary flow chart for separating portal and hepatic veins.

The real time interactive vessel separation mechanism 802 is for separating portal vein from hepatic vein. The two vein systems may be connected in the segmentation due to the partial volume effect. It is necessary to separate the two systems for further analysis such as vessel branch identification and liver lobe segmentation. An exemplary flowchart of interactive vessel separation mechanism 802 is depicted in FIG. 10.

Starting from a seed point chosen in step 901, automatic tracing may find the roots of portal and hepatic vein systems as voxels of the maximum vessel thickness in the middle and lower portion of the liver region, respectively, at step 1002. The vessel thickness of a voxel is defined as its shortest distance to the vessel boundary. The identified root points may be overlaid on images at step 1004 so that user may interactively adjust their positions at step 1008. The $1^{st}$ generation of a portal and hepatic veins may be automatically identified by growing from the portal and hepatic root points till the growing meets a branching point, at step 1006. The $1^{st}$ generation branch of a vessel system is defined as the segment from the root to the point where the vessel branches itself. The $1^{st}$ generation segments may be overlaid on images at step 1010, so that user may interactively adjust the position at step 1014. Portal branches not connected to the $1^{st}$ generation hepatic branches may be automatically labeled by tracing the sub-tree downward along each branch at step 1012. For portal branches touching hepatic vein due to the partial volume effect, a connection route and a breaking point may be automatically identified, at step 1018, as the voxel of maximum score derived from the weighted sum of a curvature and a relative intensity along the route. A relative intensity may be defined as the change of intensity from the root to the voxel under consideration. A user may adjust the breaking point position interactively at step 1022. At step 1020, a local VOI around the break point may be analyzed to automatically break connections based on a closeness measure for segment angle and for segment position. A user may interactively adjust the breaking result at step 1026. These steps may be repeated until no further connection route can be identified. The vessel separation operation ends at step 1028.

Figure 11:
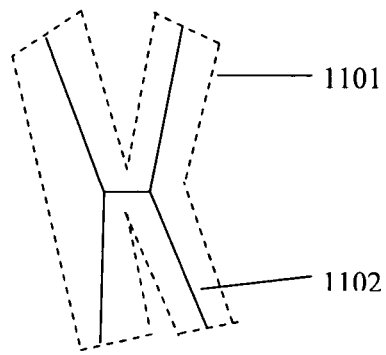
FIG. 11 illustrates an exemplary vessel branch VOI for vessel separation.
Figure 12:
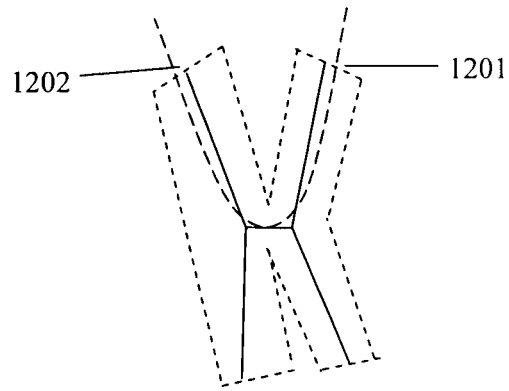
FIG. 12 illustrates exemplary entry point and ending point of a traced route.
Figure 13:
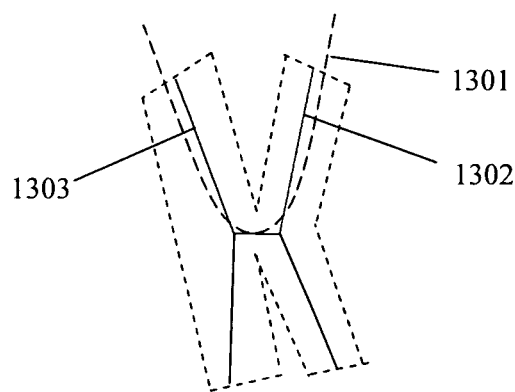
FIG. 13 illustrates an exemplary route as being classified as portal branch and hepatic branch.
Figure 14:
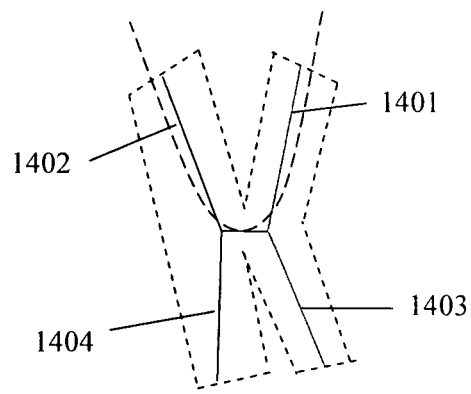
FIG. 14 illustrates an exemplary separation of other connected portal and hepatic vein branches besides a traced route.
Figure 15:
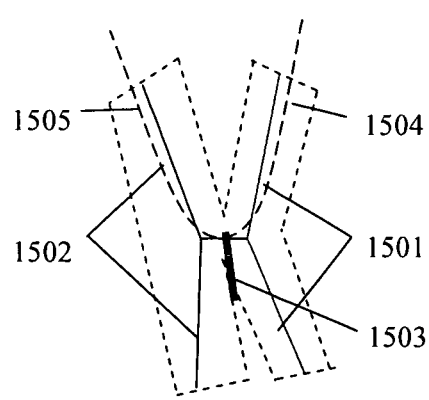
FIG. 15 illustrates an example of separating plane separating connected portal and hepatic veins.

An exemplary embodiment for the breaking operation at step 1020 is illustrated through FIGS. 11 to 16. FIG. 11 depicts an exemplary VOI at around a break point. The dashed lines 1101 are the vessel boundary, the solid lines 1102 are central lines of the vessel. A tracing from the hepatic root to the portal root may generate a curved dash line within vessel, as shown in FIG. 12. An entrance point 1201 coming from the portal root and an exit point 1202 leading to the hepatic root may be identified as the intersection points of the route with the VOI. The tracing route 1301, as shown in FIG. 13, may be compared with the center lines. A closeness measure of the center line segments 1302 and 1303 to the route 1301 may be used to make a decision that segment 1302 belongs to portal vein and segment 1303 belongs to hepatic vein. As illustrated in FIG. 14, to determine the assignment of segments 1403, the angles and the end-point distances between 1403 and 1401, and between 1403 and 1402 may be computed. A closeness measure may be derived based on a weighted sum of the angle and distance. The minimum of the closeness measures may be chosen decide whether segment 1403 belongs to 1401 or 1402. In FIG. 14, segment 1403 gives the minimum closeness measure and it is assigned to the portal vein. Similarly, segment 1404 may be determined as being from the hepatic vein. The next step is to find a cutting plane that separates all voxels in the VOI into portal voxels and hepatic voxels. As illustrated in FIG. 15, such a plane 1503 may be obtained by fitting a plane that maximizes the summed distance from the two segments 1501 and 1502 to the plane.

Figure 16:
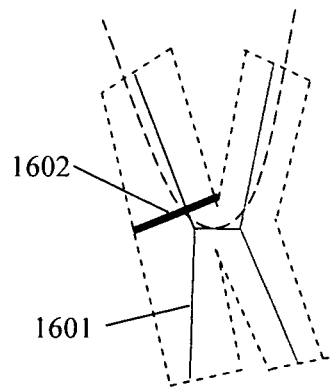
FIG. 16 illustrates an example of separation adjustment.

User correction of separation results, made at step 1206, may be illustrated through FIG. 16. In a preferred embodiment, user may click, per computer mouse, a wrongly separated segment, In FIG. 16, suppose user clicks segment 1601. After the click, a new plane may be fitted with new assignment of the clicked segment to find the new cutting plane 1602, which may be used to make a new separation of voxels in the VOI.

Figure 17:
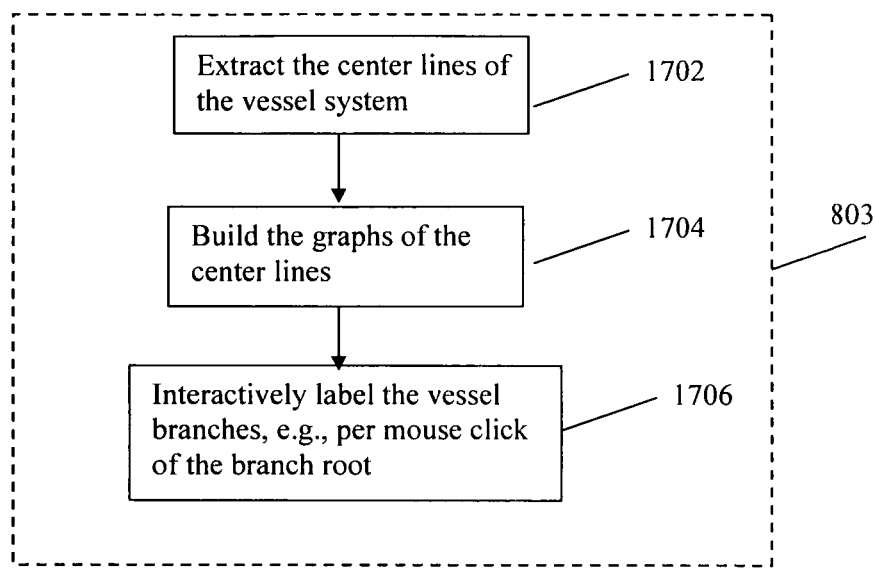
FIG. 17 illustrates an exemplary flowchart for interactive vessel labeling.
Figure 18:
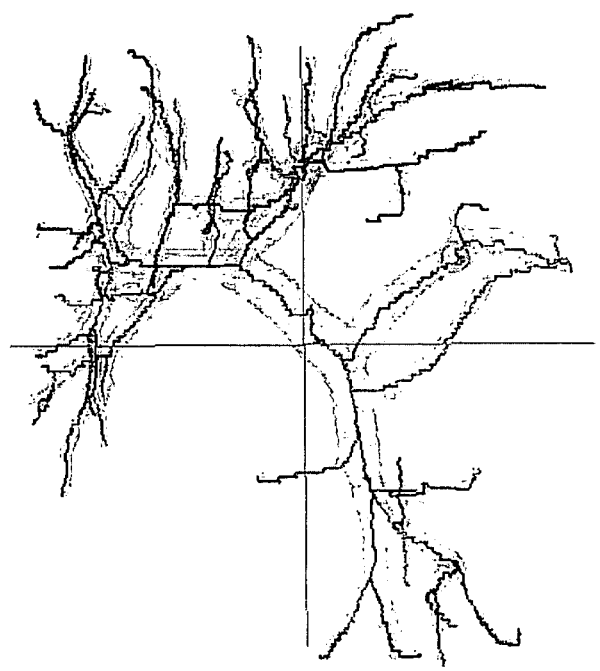
FIG. 18 illustrates an exemplary graph of a vessel system.

When connecting vessels are separated, the portal and hepatic vein systems may be labeled by the interactive vessel labeling mechanism 803. An exemplary flow chart is shown in FIG. 17. Centerlines of separated portal or hepatic vessel systems may be extracted at step 1702. Based on the extracted centerlines, graphs of portal or hepatic vein systems may be constructed at step 1704. Such graphs may comprise edges and vertexes. Each vessel segment may be represented by an edge. Branching points are vertices. FIG. 18 illustrates such an exemplary graph. Different segments of a vessel may be labeled in different color. At step 1706, a user may interactively label vessel branches. In an exemplary embodiment, a user may click on a point near the root of a branch to enable or activate automatic labeling. Other interactive operations may also be provided, for example, an existing label may be removed via, e.g., by a defined mouse click on a corresponding labeled segment. The vessel branch labeling algorithm may be applicable to both portal vein and hepatic vein systems.

Figure 19:
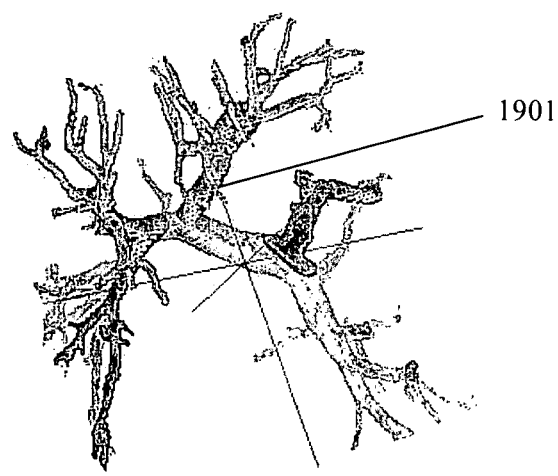
FIG. 19 illustrates an example of a labeled portal vein system.

To make interactive labeling of vessels after vessel separation, a user may click on the root of a branch. An automatic tracing may follow the paths from the clicked point to all leafs of the graph tree. The traced voxels may be assigned to the same label. FIG. 19 illustrates an example of a labeled portal vein system. A user may click on the root segment 1901 to label that branch. Subsequent vessel segments starting from the clicked point may be automatically identified by tracing in the vessel graph.

While the teaching has been described with reference to the certain illustrated embodiments, the words that have been used herein are words of description, rather than words of limitation. Changes may be made, within the purview of the appended claims, without departing from the scope and spirit of the teaching in its aspects. Although the teaching has been described herein with reference to particular structures, acts, and materials, the teaching is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

What is claimed is:

1. A method implemented on a computer having one or more processors and storage for separating vessel branches of a first vessel system from vessel branches of a second vessel system in a three dimension (3D) image, comprising the steps of:

segmenting, by vessel segmentation mechanism implemented on the one or more processors, the 3D image to obtain a plurality of vessel branches;
extracting, by vessel separation mechanism implemented on the one or more processors, a center line for each of the vessel branches;
determining, by the vessel separation mechanism, a first root point associated with the first vessel system and a second root point associated with the second vessel system;
tracing, by the vessel separation mechanism, starting from the first root point, along the vessel branches to derive a tracing path;
automatically determining, by the vessel separation mechanism, a break point along the tracing path as a voxel of maximum score derived from a weighted sum of a curvature measure of the tracing path and a relative intensity measure of the tracing path, the relative intensity measure being indicative of change of intensity from the first root point to the voxel, where the break point separates the tracing path into a first portion and a second portion;
determining, by the vessel separation mechanism, a region of interest in the 3D image based on the break point;
assigning, by the vessel separation mechanism, one or more center lines in the region of interest to either the first or the second vessel system;
automatically obtaining, by the vessel separation mechanism, a cutting plane in the region of interest by fitting a plane that maximizes a total distance from points on the center lines assigned to the first or second vessel system to the plane;
automatically constructing, by vessel labeling mechanism implemented on the one or more processors, a first and a second graph representations for the first and second vessel systems, respectively, based on the center lines assigned to each of the first and second vessel systems and the cutting plane, wherein automatically constructing comprises: extracting the center lines assigned to each of the first and second vessel systems, and constructing parts of the first and second graph representations corresponding to edges and vertexes of the first and second vessel systems, respectively; and
labeling, by the vessel labeling mechanism, one or more vessel branches in each of the first and second vessel systems with different labels based on the first and second graph representations.

2. The method of claim 1, wherein the first vessel system is a portal vessel system and the second vessel system is a hepatic vessel system.

3. The method of claim 1, wherein each of the graph representations comprises at least one edge and at least one vertex, where each edge in the graph representation represents a vessel segment and each vertex represents where two vessel segments serially connect.

4. The method of claim 3, wherein the vessel segment is a portion of a vessel branch.

5. The method of claim 1, wherein the step of labeling comprises:
visualizing the vessel system on a display;
selecting a first vessel segment of the vessel branch to be labeled;
identifying a second vessel segment, other than the first vessel segment, that belongs to the vessel branch based on the corresponding graph representation of the vessel system; and
marking the first vessel segment and the second vessel segment using a label.

6. The method of claim 5, wherein the step of selecting is performed via a mouse.

7. The method of claim 6, wherein the first vessel segment is selected by clicking the mouse at a position on the display where the first vessel segment is visualized.

8. The method of claim 5, wherein the first vessel segment corresponds to one of a plurality of vessel segments along the vessel branch and the first vessel segment has a size not smaller than that of any other vessel segment of the vessel branch.

9. The method of claim 5, wherein the step of marking using a label includes re-visualizing the vessel branch in a visualization scheme determined based on the label.

10. The method of claim 1, wherein the step of assigning comprises:
assigning a first center line in the first portion in a closest proximity with the first root point to the first vessel system;
assigning a second center line in the second portion in a closest proximity with the second root point to the second vessel system; and
assigning a center line to the first or the second vessel system based on an angle between the center line and the first or the second vessel system and a distance between a point where the center line interests a boundary of the region of interest and another point where either the first center line or the second center line intersects the boundary of the region of interest.

11. The method of claim 1, wherein the step of segmenting comprises the steps of:
selecting an initial starting point in the 3D image;
performing region growing based on the initial starting point to identify a first group of vessel candidate;
performing line filtering in the 3D image to identify a second group of vessel candidate; and
merging the first group of vessel candidate with the second group of vessel candidate to produce the plurality of vessel branches.

12. The method of claim 1, wherein the curvature measure at the break point exceeds a threshold and/or is not smaller than that of another point along the tracing path.

13. The method of claim 1, wherein the relative intensity measure at the break point exceeds a threshold.

14. The method of claim 1, further comprising making, interactively, an adjustment to get a result from the assigning step.

* * * * *